United States Patent [19]

Despotis

[11] Patent Number: 4,790,327
[45] Date of Patent: Dec. 13, 1988

[54] ENDOTRACHEAL INTUBATION DEVICE

[76] Inventor: George Despotis, 5320 N. Sheridan Rd., Apt. 806, Chicago, Ill. 60640

[21] Appl. No.: 78,256

[22] Filed: Jul. 27, 1987

[51] Int. Cl.$^4$ .......................................... A61M 16/00
[52] U.S. Cl. ................ 128/719; 128/205.23; 128/207.16; 422/85
[58] Field of Search .............. 128/207.14, 207.15, 128/207.17, 205.23, 719, 207.16; 436/133; 422/85, 55, 56, 58

[56] References Cited

U.S. PATENT DOCUMENTS

| | | | |
|---|---|---|---|
| 2,890,177 | 6/1959 | Kilmer | 436/133 |
| 4,619,269 | 10/1986 | Cutler et al. | 128/205.23 |
| 4,691,701 | 9/1987 | Williams | 128/207.14 X |
| 4,728,499 | 3/1988 | Fehder | 128/207.14 X |

Primary Examiner—A. Michael Chambers
Assistant Examiner—John C. Fox
Attorney, Agent, or Firm—Mason, Kolehmainen, Rathburn & Wyss

[57] ABSTRACT

An endotracheal intubation device for determining correct placement of an endotracheal tube in the trachea, or windpipe, of a medical patient by detecting the presence of carbon dioxide in expired air. The portable, reusable endotracheal intubation device includes a material capable of physically and/or chemically interacting with carbon dioxide, such as barium hydroxide or calcium oxide, and a visual indicating material, such as an acid-base indicator that changes color in relation to pH changes, like ethyl violet or thymolphthalein, whereby the visual indicating material changes color in response to the interaction of the carbon dioxide with the interactant material. The visual color change of the chemical reagent materials present in the endotracheal intubation device confirms the placement of the endotracheal tube within the trachea as opposed to within the esophagus.

42 Claims, 2 Drawing Sheets

ENDOTRACHEAL INTUBATION DEVICE

BACKGROUND OF THE INVENTION

1. Field of the Invention

The present invention relates to an endotracheal intubation device that verifies placement of the endotracheal tube in the trachea, or windpipe, of a medical patient. More particularly, the endotracheal intubation device includes a suitable carbon dioxide absorbent that can physically and/or chemically interact with the carbon dioxide and a suitable visual indicator for detecting carbon dioxide absorption. By attaching the endotracheal intubation device to an endotracheal tube, placement of the endotracheal tube within the trachea, as opposed to within the esophagus, is verified by visually observing the color change of the chemical reagents, comprised of the carbon dioxide absorbent and the visual indicator. The incorrect placement of the endotracheal tube into the esophagus will not produce the visual color change because the carbon dioxide, present in the exhalations of the patient, is not available to contact the indicator treated carbon dioxide absorbent.

2. Description of the Prior Art

Endotracheal intubation is a routinely performed procedure, and one of the first techniques taught to the anesthesia trainee. Today the technique is performed by individuals having different backgrounds and levels of training in the operating suite, emergency room, intensive care unit, hospital ward and in the field.

However, the frequency of tracheal intubation in modern anesthetic practices belies its importance. Although endotracheal intubation is performed routinely in anesthesia, endotracheal intubation is a dangerous procedure and often does not receive the respect and attention it deserves. Anesthetic-related disability and mortality statistics indicate that unrecognized esophageal intubation, as opposed to endotracheal intubation, remains a problem, even among anesthesia personnel specifically trained in such a procedure.

Undiagnosed esophageal intubation continues to figure predominantly in anesthesia related morbidity and mortality. Birmingham, et al., in *Anesth Analg.*, Vol. 65, page 886 to 891 (1986), reviews the various detection techniques for differentiating between endotracheal and esophageal tube placement, and found that most of the commonly utilized methods of verifying tube position have been shown to fail under certain circumstances.

The verification of correct tube placement within the trachea is a major problem for anesthesia and emergency personnel involved in endotracheal intubation. Both in surgical and emergency situations, intubation of the trachea often is necessary because normal airway protective reflexes have been lost, and therefore, tracheal intubation is required both to protect against aspiration of stomach contents and for ventilation.

However, because of the human anatomy, an attempt at endotracheal intubation may easily result in esophageal intubation. The anatomic proximity of the trachea and the esophagus facilitates inadvertent esophageal intubation during certain circumstances. For example the standard method of determining correct tube placement is visualization of the vocal chords. However, when the vocal chords cannot be visualized due to an atypical anatomy, excessive excretions or poor laryngoscopy technique by inexperienced personnel, verification of proper tube placement is essential. In addition, although the trachea may have been correctly intubated initially, during CPR (cardiopulmonary resucitation), involving relatively large chest movement of the patient, tracheal tube migration may occur with resultant extubation.

The overall result of esophageal intubation, or inadvertent endotracheal extubation, is the direct failure of both preventing aspiration of stomach contents and protecting the airway that provides ventilation for the patient. Therefore, the consequences are the aspiration of stomach contents, resulting in pneumonia, and the lack of ventilation, leading to brain damage and death unless endotracheal tube placement is quickly remedied.

A number of clinical tests, as discussed in the Birmingham et al. publication, are available to verify proper tube placement within the trachea. Among the several clinical tests discussed, actual visualization of the endotracheal tube passing the vocal chords is of primary clinical importance. However, neither this test nor any of the other clinical tests is fail-safe. It has been found however that the most definitive verification of correct tube placement involves an analysis for carbon dioxide gas including end-tidal carbon dioxide devices, in combination with mass spectometric carbon dioxide analysis.

During normal ventilation, oxygen inhalation provides oxygen for normal metabolic needs. When the metabolic by-products, predominantly carbon dioxide, are moved by exhalation, the end-tidal and mass spectometric techniques afford the medical practitioner both qualitative and quantitative evaluation of the exhaled gases, including the gas of primary concern, carbon dioxide.

At present, end-tidal carbon dioxide measurement is the most reliable means of determining proper tube position and is routinely employed when possible. However, the instruments utilized in these techniques are both extremely expensive and cumbersome in size. As a result, although Eichhorn et al., in *JAMA*, Vol. 256, Issue 8, pages 1017 to 1020, have deemed carbon dioxide analysis as one of the standards of medical care, many present-day operating rooms and clinics are not equipped with these carbon dioxide detection devices.

Several investigators have attempted to make verification of endotracheal tube placement both accurate and inexpensive. In Russian Pat. No. 157,059, an endotracheal device is disclosed that includes a whistle to verify that the tube is actually inserted in the trachea and not in the gullet. The whistle serves to give out a sound during exhalation and inhalation thereby confirming the presence of the tube in the trachea. The lack of a sound indicates that the tube has been placed within the esophagus as opposed to the trachea. However, this device has several drawbacks including sound generation by stomach gases, therefore giving a false positive placement of the tube; a device that can be clogged by secretions; a device and method that most likely is ineffective on a collapsed lung; a method that relies on the increase in thoracic gas pressure and not upon the analysis of an end-tidal gas, thereby requiring a disconnect from the ventilator or the stopping of cardiopulmonary resucitation to check for correct placement; and a device that is not reusable.

Gallagher, in U.S. Pat. No. 3,373,735, discloses a medical-surgical tube including a color change acid-based indicator, such that placement of the tube through the patient's nostrils into the patient's stomach can be verified. The placement of the tube within the stomach is verified by the color change of the indicator in response to the low stomach pH of approximately 1 to 2. Incorrect placement of the tube in the lungs will not produce the color change because the pH range in the lungs varies from approximately 7.45 to approximately 8.15. This device also suffers from serious drawbacks including the need for the sometimes absent secretions to cause a pH change, as opposed to analyzing an always present gas. In addition, incorrect results can occur because of secretions having a low pH being aspirated into the trachea or lungs. Other disadvantages include the possibility of clogging, the need to disconnect the ventilating device, the device is not reusable and the possibility of trauma due to the deep insertion of the device.

McCormick, in U.S. Pat. No. 4,431,005, discloses a method and apparatus for determining the position of a device within biological tissue by using an electromagnetic detecting device. This type of device suffers from the disadvantages of being fragile, expensive and stationary as opposed to portable. Furthermore, the method will only verify the height of the tube within the biological tissue, but not the depth of the tube within the biological tissue. Therefore, the method is potentially insufficiently accurate to distinguish between tracheal and esophageal placement.

British Pat. No. 345,672 discloses the use of an absorbent, containing a visual indicator, for detecting and for removing the water vapor in air or a gas. When the absorbent changes color, the absorbent is saturated with water vapor, indicating that fresh absorbent should be added to the device in order to keep the air or gas dry.

From the scope of the prior art, it is apparent that there is a need for a device that accurately and quickly verifies the correct placement of an endotracheal tube within the trachea both at the time of initial placement and at any time thereafter during treatment. Although some such devices are presently available, they are expensive, bulky and require trained personnel for proper usage. Therefore, for small hospitals, clinics, private physicians and emergency personnel, such as paramedics, it would be highly desirable to have an economical, reusable and portable device that quickly and accurately verifies correct endotracheal tube placement that can be used by either highly trained or relatively untrained medical personnel.

SUMMARY OF THE INVENTION

Therefore, it is an object of the present invention to provide an endotracheal intubation device useful in verifying the correct placement of endotracheal tube within the trachea.

Another object of the present invention is to provide an endotracheal intubation device that eliminates or minimizes errors in placement of the endotracheal tube during surgical or emergency treatment.

Another object of the present invention is to provide an endotracheal intubation device that eliminates the possibility of giving an incorrect verification of endotracheal tube placement within the trachea.

Another object of the present invention is to provide an endotracheal intubation device that verifies both correct initial endotracheal tube placement and correct tube placement throughout the entire medical procedure without the need to interrupt the procedure and to recheck for the correct tube placement.

Another object of the present invention is to provide an endotracheal intubation device that verifies correct endotracheal tube placement by analyzing the exhalations of the medical placement for the presence of carbon dioxide.

Another object of the present invention is to provide an endotracheal intubation device that analyzes the exhalations of the patient for carbon dioxide by a physical and/or chemical interaction of the carbon dioxide with an absorbent that changes pH in response to carbon dioxide absorption, and therefore induces a color change in a visual indicator.

Another object of the present invention is to provide an endotracheal intubation device that can be used in hospitals, clinics, physician's offices and ambulances to qualitatively check patient exhalations for carbon dioxide, and therefore verify correct endotracheal tube placement within the trachea.

Another object of the present invention is to provide an endotracheal intubation device that can be used by highly trained medical personnel or by relatively untrained emergency personnel.

Still another object of the present invention is to provide an endotracheal intubation device that is economical, portable and reusable.

In brief, the present invention is directed to an endotracheal intubation device that overcomes the disadvantages of the prior art systems in verifying the correct placement of the endotracheal tube within the trachea, as opposed to within the esophagus. The present invention is used for prompt and accurate determination of endotracheal tube placement, thereby reducing the frequency of anesthetic accidents resulting in death or cerebral damage because of faulty placement of the endotracheal tube during surgery or emergency treatments.

More particularly, the present invention is directed to an endotracheal intubation device that can be attached to the endotracheal tube and to a ventilator such as an Ambu-bag, and that can be used to verify correct endotracheal tube placement within the trachea. The device includes a chemical reagent comprising a carbon dioxide absorbent, such as barium hydroxide or calcium oxide, and a visual indicator, such as ethyl violet or thymolphthalein, to physically and/or chemically ineract with carbon dioxide exhaled by the patient and cause a color change in response to a pH change caused by carbon dioxide ineraction with the absorbent. A color change by the absorbent verifies endotracheal tube placement, while the absence of a color change indicates placement within the esophagus. Esophageal placement precludes patient exhalation of carbon dioxide through the endotracheal tube device of the present invention, thereby making carbon dioxide contact with the absorbent in the color change impossible.

BRIEF DESCRIPTION OF THE DRAWING

These and other objects and advantages of the present invention will become readily apparent upon consideration of the following detailed description and attached drawing wherein.

DETAILED DESCRIPTION

The invention relates in general to a portable endotracheal intubation device adapted to be used by physicians, paramedics and the like to continuously verify the correct placement of an endotracheal device within the trachea of a patient when other expensive equipment, such as an end-tidal device or a mass spectrometer, is not available. The correct placement of the endotracheal tube in the trachea of a patient is verified by detecting for presence of carbon dioxide at the proximal end of the endotracheal tube, which extends from the breathing passageway of a patient. The endotracheal intubation device of the present invention is further adapted to provide continuous monitoring of the endotracheal tube to detect for migration of the endotracheal tube from the trachea, which may occur during various circumstances, such as during cardiopulmonary resuscitation.

Figures 1A, 1B, 2, 3, 4, 5:
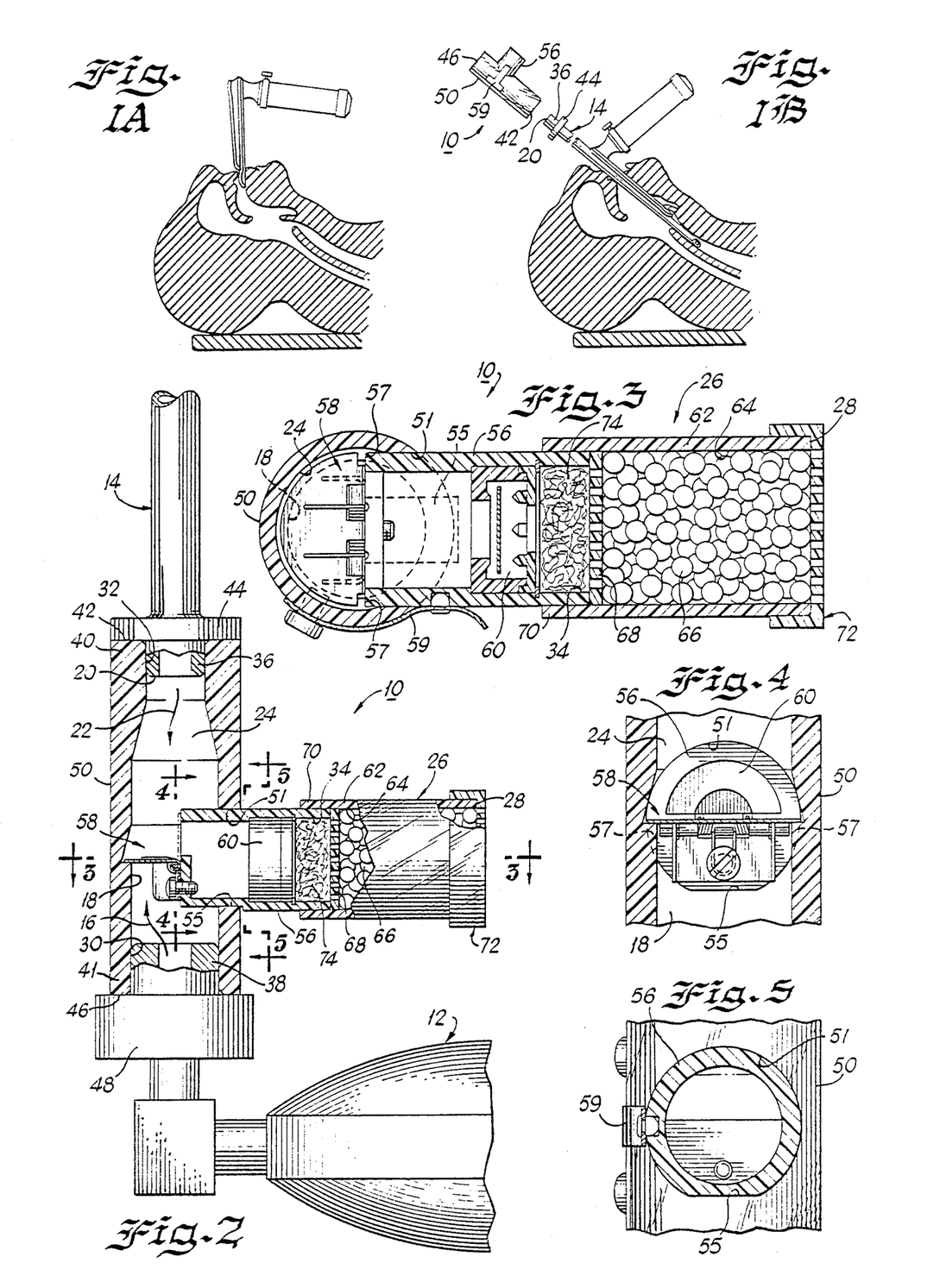
FIG. 1A is a cross-section of a patient's head and throat illustrating the esophagus and trachea at the initial stage of laryngoscopy.
FIG. 1B is a cross-section of a patient's head and throat illustrating the esophagus and trachea at a final stage of laryngoscopy.
FIG. 2 is a sectional view of the endotracheal intubation device of the present invention connected to a source of supply air and an endotracheal tube.
FIG. 3 is a plan view of the endotracheal device taken along lines 3—3 of FIG. 2.
FIG. 4 is a cross-sectional view of the endotrachael device taken along lines 4—4 of FIG. 2.
FIG. 5 is a cross-sectional view of the endotracheal device taken along lines 5—5 of FIG. 2.

Referring to the drawing, FIGS. 1A and 1B illustrate the trachea and esophagus of a patient during the initial and final stages of laryngoscopy, respectively. A laryngoscope may be used to facilitate endotracheal intubation by providing a guide channel from the mouth to the trachea through which an endotracheal tube may be inserted. However, due to the close proximity of the trachea and the esophagus, inadvertant esophageal intubation may occur due to various anatomical factors or due to the lack of experience of the person performing the laryngoscopy. Oftentimes, correct placement of endotracheal intubation must be verified by emergency medical technicians in an ambulance or other location where there is no access to a conventional machine, such as an end-tidal device or a mass spectrometer. The present invention provides a portable, inexpensive, reliable and continuous method to verify endotracheal intubation.

Referring to FIG. 2, the endotracheal intubation device of the present invention is generally identified by the reference numeral 10. This device is inserted between a source of air 12, such as an Ambu-bag or an air turbine (not shown) and an endotracheal tube 14. During inhalation, artificial respiration air is supplied from the source of air supply 12 through an inhalation air passageway 18 in the endotracheal intubation device 10 to the proximal end 20 of the endotracheal tube 14 in the direction indicated by the arrow 16. During exhalation, air flows in the direction of the arrow 22 through the exhalation air passageway 24 and passes through a visual indicator 26, which analyzes for the presence of carbon dioxide, before being vented to the atmosphere. Thus, if the presence of carbon dioxide is indicated by the visual indicator 26, correct placement of the endotracheal tube in the trachea is verified.

The endotracheal intubation device 10 of the present invention is comprised of generally a tubular device having three ports; an air supply port 30, a patient port 32 and an exhalation port 34. The patient port 32 and the air supply port 30 are adapted to mate with standard size male connectors of an endotracheal tube 14 and an air supply source, such as an Ambu-bag 12, respectively. Specifically, the inner diameter of the patient port 32 may be formed to be 15 mm in diameter to mate with an endotracheal tube having a male connector sleeve 36 with an outer diameter 15 mm, while the air supply port 30 may be formed to mate with a 22 mm diameter Ambu-bag male connector sleeve 38. The different size diameters for the air supply port 30 and the patient port 32 may be effected either by forming the endotracheal intubation device 10 with a non-uniform wall thickness as shown in FIG. 2 or by using an intermediate connector (not shown) between the patient port 30 and the Ambu-bag 12 and between the patient port 32 and the endotracheal tube 14.

In the embodiment illustrated in FIG. 2, the thickness of the wall 40 of the endotracheal intubation device 10 is greater at the patient port 32 than at the air supply port 32 because of the smaller inner diameter required at the patient port 32. The thicker wall portion 40 at the patent port 32 defines an annular shoulder 42 for seating against flange 44 at the proximal end 20 of the endotracheal tube 14. The connection between the male connector sleeve 36 at proximal end 20 of the endotracheal tube 14 and the patient port 32 may be either threaded or a friction fit to provide an airtight connection therebetween. The wall portion 41 proximate of the air supply port 30 also defines an annular shoulder 46 for seating against a flange 48 on the Ambu-bag 12. The connection may be either threaded or a compression fit to provide an airtight connection between the Ambu-bag 12 and the air supply port 30.

The endotracheal intubation device 10 in accordance with the present invention is comprised of a first tubular member 50 and a second tubular member 56. The first tubular member defines an air supply port 30 at one end and a patient port 32 at the other end. The first tubular member 50 also defines an inhalation air passageway 18 disposed between the patient port 32 and the air supply port 30 which allows air communication between the source of air 12 and the endotracheal tube 14. As will be described in detail below, the first tubular member 50 also defines a portion of an exhalation air passageway 24 by providing a passageway between the endotracheal tube 14 to the exhalation port. A circular aperture 51 (FIG. 7) in the wall of the first tubular member 50 is adapted to receive a second tubular member 56 27 such that the longitudinal axis of the first tubular member 50 is substantially perpendicular to the longitudinal axis of the second tubular member 56. A flat 55 (FIGS. 4 and 5) may be used to insure proper orientation of the first intubular member 50 with respect to the second intubular member 56. A flange 57 formed integral with the second tubular member 56 seats against the exterior wall of the first tubular member 46, thus allowing the second tubular member 56 to be in communication with the patient port 32 via a portion of the first tubular member 50, which together define an exhalation air passageway 24 between the proximal end 20 of the endotracheal tube 14 and the exhalation port 34. A bracket 59 (FIGS. 6 and 7) may be used to secure the first tubular member 50 to the second tubular member 56.

In order to direct the exhaled air through the exhalation air passageway 24, a diverter valve 58 (FIGS. 2-5) is disposed within the first tubular member 50, which is responsive to air flow in the direction of the arrow 16, to close the end of the second tubular member 56 and, consequently, the exhalation port 34 during inhalation. During exhalation, the diverter valve 58 is spring biased to close the air supply port 30 to preclude exhaled air from backflowing into the air supply 12 during exhalation. A check valve 60 (FIGS. 2, 3 and 8) may be provided within the second tubular member 56 to prevent inhalation through the second tubular member 56 in the event of a spontaneous breath by the patient during an exhalation cycle (e.g., when there is no air flow from the source of air supply 12). The aforementioned combination of the tubular members 50 and 56 and cooperating valves 58 and 60 define a manifold for providing an inhalation air passageway 18 and an exhalation air passageway 24. Such manifolds are known in the art as non-rebreathing valves and are available from Instrumentation Industries in Bethel Park, Pa.

Figures 6, 7, 8, 9, 10, 11:
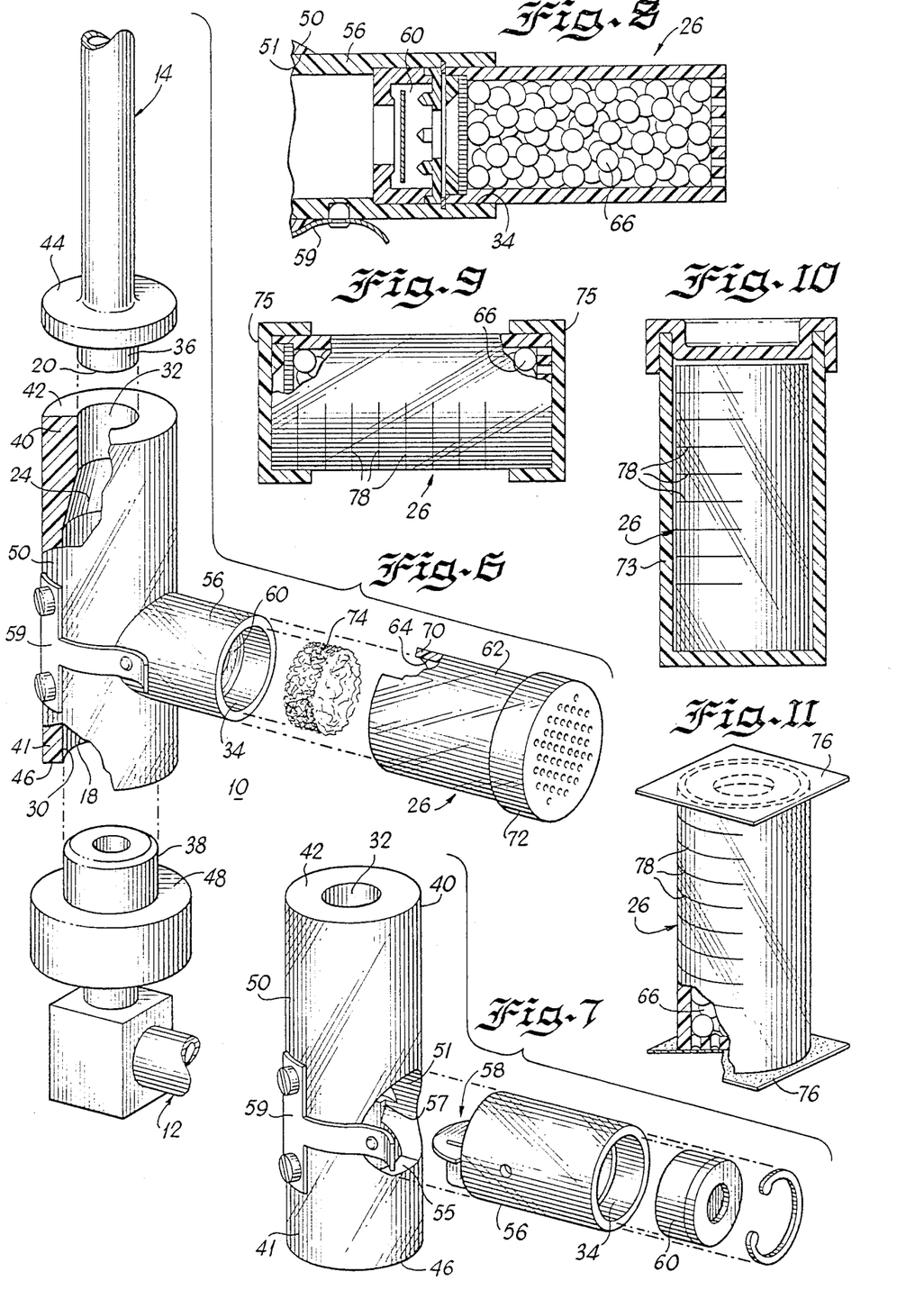
FIG. 6 is an exploded perspective view of the endotracheal device in accordance with the present invention.
FIG. 7 is an exploded perspective view of an air manifold which forms a portion of the endotracheal intubation device in accordance with the present invention.
FIG. 8 is a fragmentary plan view of an alternative embodiment of the visual indicator illustrated in FIG. 3.
FIG. 9 is a plan view of another alternative embodiment of the visual indicator illustrated in FIG. 3 shown with airtight end caps.
FIG. 10 is a plan view of yet another alternative embodiment of the visual indicator illustrated in FIG. 3, shown encapsulated in an airtight container.
FIG. 11 is a plan view of still another alternative embodiment of the visual indicator illustrated in FIG. 3, shown with the end caps sealed with tape.

As shown in FIGS. 2, 3 and 6, the visual indicator 26 is connected to the distal end 61 of the tubular member 56 and is comprised of a tubular member 62 which defines a cylindrical cavity 64 for receiving a chemical reagent 66 for indicating the presence of carbon dioxide. An end cap 68, disposed inside and intermediate one end of the tubular member 62, defines a female connector 70 for connection to the exhalation port 34. The inner diameter of the tubular member 56 is sized to be received into the female connector 70. By utilizing larger diameter for the visual indicator 26, the air flow resistance is decreased from the inhalation port 34 to mitigate the flow resistance caused by the chemical reagent 66 within the visual indicator 26. Alternatively, as shown in FIG. 8, the outer diameter of the visual indicator 26 may be made smaller than the diameter of the tubular member 56 to be received therewithin. With either embodiment, the connection between the second tubular member 56 and the visual indicator 26 may be by friction fit or by threaded connection. The end cap 68, among other things, limits the travel of the second tubular member 56 within the female connector 70 of the visual indicator 26. Another end cap 72 is disposed at the other end of the tubular member 62 of the visual indicator 26 defining a cavity 64 for receiving the chemical reagent 66. Each of the end caps 68 and 72 are air permeable to allow expired air to pass from the patient through visual indicator 26 containing the chemical reagent 66 to the atmosphere. The end cap 68 may be formed integral with the tubular member 62 or may be formed separately and secured to the inner wall thereof with an appropriate adhesive or by ultrasonic welding. The end cap 72 is formed separately and affixed to the tubular member 62 after the chemical reagent 66 has been placed in the cylindrical cavity 64 within the indicator 26.

A filter 74 is preferably disposed between the end cap 68 and the second valve 60 to prevent inhalation of dust from the chemical reagent 66. The filter 74 may be disposed either within the visual indicator 26 or within the tubular member 56. The filter 74 may be comprised of any non-toxic material that both prevents the inhalation of dust and does not restrict the exhalations of the patient. The filters can be made of glass wool, loosely-packed cotton, loosely-packed filter paper and other like materials.

In the embodiment illustrated in FIGS. 2, 3 and 6, the visual indicator 26 is removable from the second tubular member 56. However, it will be appreciated by those of ordinary skill in the art, the principles of the invention are equally applicable to an endotracheal intubation device 10 formed with an integrally formed visual indicator 26. However, there are several advantages of using a removable visual indicator 26. First, the visual indicator 26 can be easily removed allowing the exhalation port 34 to be easily connected to an end-tidal device and a mass spectrometer, or the like, once the patient arrives at the hospital for continuous quantitative and qualitative carbon dioxide analysis. Secondly, the visual indicator 26 can be either regenerated or discarded allowing the non-rebreathing valve to be autoclaved or otherwise sterilized and reused.

In order to prevent the chemical reagent 66 from being actuated prior to being placed in use, the chemical reagent 66 must be protected from the atmosphere This can be accomplished in a number of different ways. For example, the visual indicator 26 may be packaged in an airtight container 73 (FIG. 10) or by providing removable solid end caps 75 (FIG. 9) that are adapted to be removed prior to use. If the visual indicator 26 is sealed with removable solid end caps 75, the end cap 72 must be disposed inside the tubular member 62, similar to the other end cap 68, to allow the removable solid end cap to be fit on the outside of the tubular member 62. The visual indicator 26 may also be sealed with tape 76 as shown in FIG. 11.

Regarding the chemical reagent 66, various chemical reagents are adapted to be within the breadth and scope of the present invention. For example, in one embodiment, the chemical reagent comprises calcium oxide and thymolphthalein on an inert support such as sand and/or glass beads. In this embodiment, the exhaled carbon dioxide contacts and is physically and/or chemically absorbed by the calcium oxide. The resulting ineraction produces a pH change that changes the color of the chemical reagents from blue to white. In another embodiment, the chemical reagents comprise barium hydroxide and ethyl violet on a suitable support. In this embodiment, the presence of carbon dioxide, and therefore verification of the endotracheal tube within the trachea, is seen in a color change of white to purple.

In general, the chemical reagents of the present invention can be any compound that absorbs and reacts with the gaseous carbon dioxide, thereby producing a pH change and a color change in the visual indicator. Because of the slightly acidic nature of carbon dioxide, the carbon dioxide-absorbing chemical is usually alkaline in nature in order to ensure a rapid and total reaction with carbon dioxide, and to ensure a sufficient pH change to change the color of the visual indicator. The carbon dioxide absorbent compounds that can be used in the device of the present invention include the oxides and hydroxides of the alkali metals and alkaline earth metals, such as barium oxide, barium hydroxide, calcium oxide, calcium hydroxide, sodium hydroxide, magnesium oxide, potassium hydroxide, lithium hydroxide and combinations thereof. Similarly amphoteric oxides or hydroxides of the transition metals that can react with carbon dioxide, such as zinc oxide, can also be used either alone or in combination with the alkali metal and alkaline earth oxides and hydroxides. Similarly, commercially available hydrazinc compounds, such as those used in the Drager tube atmosphere analyzing device, available from Dragerwerk A.G., Lubeck, Germany, can be used in accordance with the present invention.

A visual indicator also must be included in the device of the present invention in order to visually detect the interaction of the exhaled carbon dioxide with the carbon dioxide absorbing compound. The indicator will change color in relation to a pH change that occurs when the carbon dioxide absorbing compound react with the exhaled carbon dioxide. Normally, the visual indicator will exhibit its alkaline color within the device of the present invention until the carbon dioxide contacts and reacts with the absorbent compound, causing a chemical reaction and pH drop. The visual indicator will then change color to its acidic color. The particular visual indicator to be used will vary according to the absorbent compound used; however, indicators normally changing color in a pH range of about 8 to about 11.5, and preferably in a pH range of about 9 to about 10.5, can be used in the device of the present invention. These visual indicators include ethyl violet, thymolphthalein, alizarin yellow, phenolphthalein, thymol blue, ethyl bis(2,4-dimethylphenol)acetate, p-naphthol benzene, o-cresolphthalein and alizarin. Graduations 78 (FIG. 9) may be disposed on the tubular member 62 to prove a quantitative indication of carbon dioxide.

The analysis of exhaled carbon dioxide by either conventional capnographs, mass spectrometry or the proposed portable method which has been described has limitations. First, during low cardiac output states, such as during cardiac arrest circumstances and diagnosed pulmonary embolus, the perfusion of the pulmonary circulation is compromised leading to a lower than normal value for exhaled carbon dioxide, ranging from 20–30 Tor., as opposed to a normal 40 Tor. In addition, patients that have had a cardiac arrest usually are ventilated by mouth-to-mouth or by mask prior to intubation, which may result in a small amount of carbon dioxide within the stomach or the esophagus. This could potentially result in a false positive result by any form of exhaled carbon dioxide analysis. The carbon dioxide concentrations in this circumstance would be extremely low (e.g. 5–10 Tor.) and would approach zero within a few breaths. The addition of the graduations 78 give a quantitative analysis which delineates correct endotracheal tube placement in the circumstances stated above. If there is a questionable result, another reagent cartridge can be inserted to reaffirm endotracheal tube placement.

All the materials used to make the endotracheal intubation device, of course, must be made from a non-toxic and inert material, such as polycarbonate, PVC or other suitable materials. The materials should also be suitable for autoclaving and other sterilization techniques.

In operation, following laryngoscopy, the endotracheal tube is inserted into the trachea of the patient. The patient port 32 is connected to the proximal end 20 of the endotracheal tube 14 and the source of air supply 12 is connected to the air supply port 30. The visual indicator 26 is removed from its airtight container (or the airtight solid end caps or tapes are removed) and the visual indicator is connected to the exhalation port 34. Resuscitation is then commenced. As resuscitation air flows from the air supply 12 through the inhalation air passageway 18, the diverter valve 58 is forced open to allow the air to flow to the patient port 32 and into the proximal end 20 of the endotracheal tube 14. If the endotracheal tube 14 is properly inserted into the trachea, carbon dioxide will be exhaled by the patient and expelled through the endotracheal tube 14 into the patient port 32. During exhalation, the diverter valve 58 closes the inhalation port 30 under the influence of a spring and defines an exit passageway for the carbon dioxide from the patient port 32 to the visual indicator 26. The carbon dioxide reacts with the chemical agent causing a pH change resulting in a color change of the visual indicator. This indicates the presence of carbon dioxide and verifies correct placement of the endotracheal tube within the trachea. Another valve 60 in the exhalation passageway 24 prevents inhalation through the exhalation passageway 24 due to a spontaneous breathing by the patient. If the exhalation tube is in the trachea the visual indicator will so indicate.

Thus, it should be apparent that an endotracheal intubation device has been disclosed which can be used to verify the placement of an endotracheal tube within the trachea in an easy and inexpensive manner. As heretofore discussed, the system can be implemented in a number of ways, all of which are contemplated to be within the scope of the appended claims.

What is claimed and desired to be secured by Letters Patent of the United States is:

1. A portable endotracheal intubation device for verifying the correct placement of an endotracheal tube in the trachea of a patient comprising:
   an endotracheal tube having a proximal end adapted to extend from the breathing passageway of a patient and a distal end adapted to extend into the trachea of a patient;
   means for supplying air to said endotracheal tube;
   means including a patient port, air supply port and an exhalation port, adapted to be connected to said air supply means and said endotracheal tube for providing an air inhalation passageway between the patient port and said air supply port and for providing an air exhalation passage way between said patient port and said exhalation port, wherein said exhalation port is in communication with the atmosphere and is isolated from said air supply port during exhalation; and
   means serially coupled between said exhalation port and said atmosphere for providing a visual indication of the placement of the endotracheal tube in the trachea of the patient comprising a visual indicating material which changes color in the presence of carbon dioxide.

2. A portable endotracheal intubation device as recited in claim 1 wherein said visual indication means includes means for quantitatively displaying the presence of carbon dioxide.

3. An endotracheal intubation device as recited in claim 1, wherein said air supply means comprises a manually operable Ambu-bag.

4. An endotracheal intubation device as recited in claim 1 wherein said air supply means comprises a mechanically operated device.

5. An endotracheal intubation device as recited in claim 4, wherein said mechanically operated device comprises an air turbine.

6. An endotracheal intubation device for verifying the correct placement of an endotracheal tube in the trachea of a patient comprising:
an endotracheal tube having a proximal end adapted to extend from the breathing passageway of a patient and a distal end adapted to extend into the trachea of a patient;
means for supplying air to said endotracheal tube;
means including a patient port, air supply port and an exhalation port, adapted to be connected to said air supply means and said endotracheal tube for providing an air inhalation passageway between the patient port and said air supply port and for providing an air exhalation passageway between said patient port and said exhalation port;
means in communication with said exhalation port for providing a visual indication of the placement of the endotracheal tube in the trachea of the patient comprising visual indicating material which changes color in the presence of carbon dioxide; and
means for preventing air flow in the direction from the exhalation port toward the patient port.

7. An endotracheal device as recited in claim 1, further including means for preventing inhalation of particles from said visual indicating means.

8. An endotracheal intubation device for verifying the correct placement of an endotracheal tube in the trachea of a patient comprising:
an endotracheal tube having a proximal end adapted to extend from the breathing passageway of a patient and a distal end adapted to extend into the trachea of a patient;
means for supplying air to said endotracheal tube;
means including a patient port, air supply port and an exhalation port, adapted to be connected to said air supply means and said endotracheal tube for providing an air inhalation passageway between the patient port and said air supply port and for providing an air exhalation passageway between said patient port and said exhalation port;
means in communication with said exhalation port for providing a visual indication of the placement of the endotracheal tube in the trachea of the patient comprising a visual indicating material which changes color in the presence of carbon dioxide; and
a filter located between said visual indication means and said patient port to reduce inhalation of particles from said visual indicating means.

9. An endotracheal device as recited in claim 8, wherein said filter is comprised of cotton, glass wool, or filter paper.

10. An endotracheal device as recited in claim 1, wherein said visual indicating means comprises a cylindrical housing having a visual indicating material which changes color when carbon dioxide is absorbed.

11. An endotracheal device as recited in claim 10, further including removable caps for said cylindrical housing for sealing the housing and preventing reaction of the visual indicating material prior to patient use.

12. An endotracheal device as recited in claim 10, further including a removable airtight container for receiving said visual indicating means and preventing reaction of the visual indicating material prior to patient use.

13. An endotracheal device as recited in claim 10, wherein said visual indicating means is sealed with removable tape.

14. An endotracheal device as recited in claim 10, wherein said visual indicating material is selected from the group consisting of ethyl violet, thymolphthalein, alizarin yellow, phenolphthalein, thymol blue, ethyl bis(2,4-dimethylphenol)acetate, p-naphthol benzene, o-cresolphthalein and alizarin.

15. A portable endotracheal intubation device for verifying the correct placement of an endotracheal tube in the trachea of a patient comprising:
an endotracheal tube having a proximal end adapted to extend from the breathing passageway of a patient and a distal end adapted to extend into the trachea of a patient;
means for supplying air to the proximal end of said endotracheal tube;
an air manifold having an inhalation port adapted to communicate with said air supply means, a patient port adapted to be connected to the proximal end of said endotracheal tube, and an exhalation port in communication with the atmosphere, wherein said exhalation port isolated from said inhalation port during exhalation; and
a visual indicator in communication with said exhalation port which changes color in the presence of carbon dioxide.

16. An endotracheal intubation device for verifying the correct placement of an endotracheal tube in the trachea of a patient comprising:
an endotracheal tube having a proximal end adapted to extend from the breathing passageway of a patient and a distal end adapted to extend into the trachea of a patient;
means for supplying air to the proximal end of said endotracheal tube;
an air manifold having an inhalation port adapted to communicate with said air supply means, a patient port adapted to be connected to the proximal end of said endotracheal tube and an exhalation port; and
a visual indicator in communication with said exhalation port which changes color in the presence of carbon dioxide; wherein said visual indicator comprises a cylindrical housing with air permeable end caps for containing a chemical reagent which changes color in the presence of carbon dioxide.

17. An endotracheal intubation device as recited in claim 16, wherein said visual indicator is integrally formed with said air manifold.

18. An endotracheal intubation device as recited in claim 16, wherein said visual indicator is adapted to be removably connected to said air manifold.

19. An endotracheal intubation device as recited in claim 16, wherein said visual indicator is adapted to be regenerated.

20. An endotracheal intubation device for verifying the correct placement of an endotracheal tube in the trachea of a patient comprising:
an endotracheal tube having a proximal end adapted to extend from the breathing passageway of a patient and a distal end adapted to extend into the trachea of a patient;
means for supplying air to the proximal end of said endotracheal tube;

an air manifold having an inhalation port adapted to communicate with said air supply means, a patient port adapted to be connected to the proximal end of said endotracheal tube, and an exhalation port; and a visual indicator in communication with said exhalation port which changes color in the presence of carbon dioxide.

wherein said chemical reagent comprises a carbon dioxide absorbing compound and a visual indicating material.

21. The endotracheal intubation device as recited in claim 20, wherein the carbon dioxide absorbing compound is selected from the group consisting of the alkali metal hydroxide, alkaline earth hydroxide, alkaline earth oxide, amphoteric transition metal oxides and combinations thereof.

22. An endotracheal intubation device as recited in claim 20, wherein the carbon dioxide absorbing compound is selected from the group consisting of barium oxide, barium hydroxide, calcium oxide, calcium hydroxide, sodium hydroxide, magnesium oxide, potassium hydroxide, lithium hydroxide and combinations thereof.

23. An endotracheal intubation device as recited in claim 20, wherein the visual indicating material is selected from the group consisting of ethyl violet, thymalphthalein, alizarin yellow, phenolphthalein, thymol blue, ethyl bis(2,4-dimethylphenol)acetate, p-naphthol benzene, o-cresolphthalein and alizarin.

24. A portable endotracheal intubation device for verifying the correct placement of an endotracheal tube in the trachea of a patient adapted to be connected between an endotracheal tube and a resuscitator air bag comprising:
an air manifold for providing an inhalation air passageway between the resuscitator air bag and the endotracheal tube and for providing an exhalation air passageway between said endotracheal tube and the atmosphere, wherein said exhalation passageway is isolated from at least a portion of said air passageway during exhalation; and
a visual indicator in communication with said exhalation air passageway which indicates the presence of carbon dioxide.

25. An endotracheal intubation device as recited in claim 24, wherein said air manifold and said visual indicator are formed as a one-piece assembly.

26. An endotracheal intubation device as recited in claim 25, further including means for preventing actuation of said visual indicator prior to patient use.

27. An endotracheal intubation device as recited in claim 26, further includes a removable airtight housing adapted to receive said endotracheal intubation device for preventing actuation of said visual indicator prior to patient use.

28. An endotracheal intubation device as recited in claim 24, wherein said manifold comprises two tubes connected together to form an inhalation air passageway and an inhalation air passageway.

29. An endotracheal intubation device as recited in claim 28, wherein at least a portion of said inhalation air passageway is common with said exhalation air passageway.

30. An endotracheal intubation device for verifying the correct placement of an endotracheal tube in the trachea of a patient adapted to be connected between an endotracheal tube and a resuscitator air bag comprising:

an air manifold for providing an inhalation air passageway between the resuscitator air bag and the endotracheal tube and for providing an exhalation air passageway between said endotracheal tube and the atmosphere; and a visual indicator in communication with said exhalation air passageway which indicates the presence of carbon dioxide;

wherein said air manifold includes a first tubular member, which defines a first air passageway having an air supply port at one end and a patient port at the other end, and a second tubular member which is disposed intermediate the ends of said first tubular member so as to be in communication with the air passageway of the first tubular member.

31. An endotracheal intubation device as recited in claim 30, wherein the longitudinal axis of said first tubular member and said second tubular member are not parallel.

32. An endotracheal intubation device as recited in claim 31, wherein the axis of said first tubular member and the axis of said second tubular member are substantially perpendicular.

33. An endotracheal intubation device as recited in claim 30, wherein at least a portion of said second tubular member extends beyond the inner wall of said first tubular member.

34. An endotracheal intubation device as recited in claim 30, further including an inhalation valve having a first operative position wherein the valve closes the exhalation port opening of the second tube which extends into the first air passageway in response to air flow in the direction from said air supply port to said patient port and a second operative position which closes the air supply port in response to air flow in the direction from the patient port to the exhalation port.

35. An endotracheal intubation device as recited in claim 30, further including an exhalation valve wherein the valve closes the exhalation port in response to air flow in the direction from the exhalation port to the patient port.

36. A portable endotracheal intubation device for verifying the correct placement of an endotracheal tube in the trachea of a patient comprising:
a non-rebreathing valve having an air supply port, a patient port adapted to be connected to a source of air supply and an endotracheal tube, and an exhalation port which is isolated from said air supply port during exhalation; and
a visual indicator device in communication with said exhalation port which changes color in the presence of carbon dioxide.

37. An endotracheal intubation device for verifying the correct placement of an endotracheal tube in the trachea of a patient comprising:
a non-rebreathing valve having an air supply port, a patient port adapted to be connected to a source of air supply and an endotracheal tube, and an exhalation port; and
a visual indicator device in communication with said exhalation port which changes color in the presence of carbon dioxide;
wherein said indicator device comprises a hollow cylindrical member having air permeable end caps which define a chamber for receiving a chemical reagent which changes color in the presence of carbon dioxide.

38. An endotracheal intubation device for verifying the correct placement of an endotracheal tube in the trachea of a patient comprising:
- a non-rebreathing valve having an air supply port, a patient port adapted to be connected to a source of air supply and an endotracheal tube, and an exhalation port; and
- a visual indicator device in communication with said exhalation port which changes color in the presence of carbon dioxide;
- wherein said non-rebreathing valve and said indicator device are integrally formed such that said indicator device is integrally coupled to said exhalation port.

39. An endotracheal device as recited in claim 38, further including a removable end cap adapted to close the patient port, air supply port and the inhalation port to prevent actuation of the visual indicator device prior to patient use.

40. An endotracheal intubation device as recited in claim 36, wherein said visual indicator device is removable from said non-rebreathing valve.

41. An endotracheal intubation device as recited in claim 40, further including removable end caps for preventing actuation of said indicator device prior to patient use.

42. An endotracheal intubation device as recited in claim 40, wherein said visual indicator device is regenerable and adapted to be reused after regeneration.

* * * * *